(12) United States Patent
Song et al.

(10) Patent No.: US 7,022,883 B2
(45) Date of Patent: Apr. 4, 2006

(54) PREPARATION OF ARYL INTERMEDIATES

(75) Inventors: Jinhua J. Song, Hopewell Junction, NY (US); Zhulin Tan, Danbury, CT (US); Nathan K. Yee, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 290 days.

(21) Appl. No.: 10/715,029

(22) Filed: Nov. 17, 2003

(65) Prior Publication Data

US 2004/0106807 A1 Jun. 3, 2004

Related U.S. Application Data

(60) Provisional application No. 60/428,618, filed on Nov. 22, 2002.

(51) Int. Cl.
*C07C 211/00* (2006.01)
(52) U.S. Cl. .................................................... 564/387
(58) Field of Classification Search ................. 564/387
See application file for complete search history.

(56) References Cited

U.S. PATENT DOCUMENTS 6,358,945 B1   3/2002   Breitfelder et al.

OTHER PUBLICATIONS

Kitagawa, K. et al; "Halogen, Magnesium Exchange via Trialkylmagnesates for the Preparation of Aryl- and Alkenylmagnesium Reagents**"; Angew. Chem. Ing. Ed. 2000, 39, No. 14, pp. 2481-2483.

*Primary Examiner*—Taofiq Solola
*Assistant Examiner*—Robert Shiao
(74) *Attorney, Agent, or Firm*—Michael P. Morris; Mary-Ellen M. Devlin; Anthony P. Bottino

(57) ABSTRACT

Disclosed are methods of making aryl intermediate compounds of the formula (A) which are useful in the production of heteroaryl ureas,

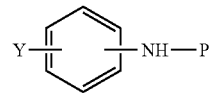

(A)

Y and P are defined herein below.

3 Claims, No Drawings

PREPARATION OF ARYL INTERMEDIATES

APPLICATION DATA

This application claims benefit to U.S. provisional application No. 60/428,618 filed Nov. 22, 2002.

FIELD OF INVENTION

This invention relates to the synthesis of aryl intermediate compounds which are useful in the production of pharmaceutically active heteroaryl urea compounds.

BACKGROUND OF THE INVENTION

Aryl- and heteroaryl-substituted ureas have been described as inhibitors of cytokine production. These inhibitors are described as effective therapeutics in cytokine-mediated diseases, including inflammatory and autoimmune diseases.

U.S. Pat. No. 6,358,945 describes cytokine inhibiting ureas of the following formula:

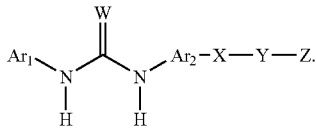

An intermediate required to prepare preferred compounds described therein has a 1,4-disubstituted naphthalene as $Ar_2$ and is illustrated in the formula below.

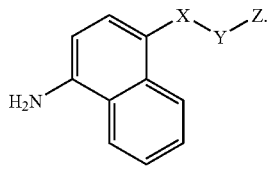

The preparation of these intermediates require the coupling of the naphthyl ring with X. Preferred X include aryl and heteroaryl groups. Previously described methods, including U.S. Pat. No. 6,358,945 achieves the coupling of these aromatic residues by using a coupling reaction catalyzed by a transition metal, such as palladium, in the presence of a ligand, such as triphenyl phosphine. Coupling methods include Stille coupling, requiring the preparation of a tributylstannyl intermediate, or a Suzuki coupling, requiring the preparation of an aryl boronic acid intermediate (Scheme I).

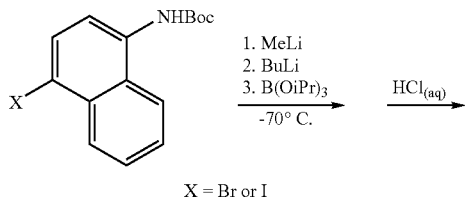

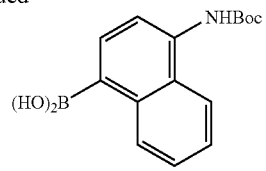

The aryl boronic acid intermediate shown in I has previously been prepared via Br—Li exchange at −70° C. It is desirable to develop a procedure without using cryogenic condition for large-scale or industrial scale production.

Kitigawa et al. disclose a method for preparing trialkyl magnesates useful for halogen-metal exchange (*Angew. Chem. Int. Ed.* 2000, 39, No. 14 2481–2483). No example in the paper implied the applicability of this method to the preparation of A, which has an acidic proton on the nitrogen.

BRIEF SUMMARY OF THE INVENTION

It is therefore an object of the invention to provide a non-cryogenic synthesis for aryl intermediate compounds such as aryl boronic acids which are useful in the production of heteroaryl urea compounds.

DETAILED DESCRIPTION OF THE INVENTION

In a broad generic aspect, there is provided a method of making a compound of the formula (A):

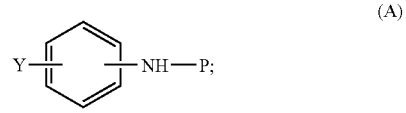

wherein the formula (A):

P is a nitrogen protecting group compatible with Grignard reagents, preferably P is chosen from Boc, Cbz, —CO$_2$Me, —Ac, -Bn; preferably P is Boc;

Y is chosen from —B(OH)$_2$, —CHR'—OH, —CR'$_2$—OH, alkyl, alkene and acyl;

E is an electrophile as defined herein below;

the phenyl ring in (A) is optionally benzo-fused to form naphthyl wherein substituents Y or NH—P can be independently at any position on each of the one or two rings, where the phenyl is not benzo-fused substitution can be para, meta or ortho, preferably para; preferably formula (A) is

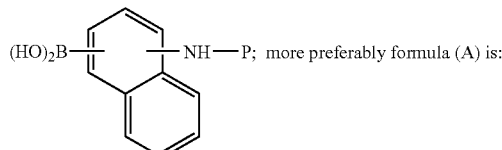

more preferably formula (A) is:

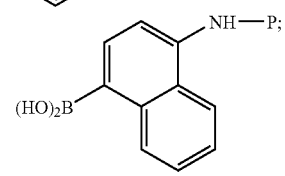

said method comprising, in a one pot reaction:

reacting a compound of the formula (B) with 2 equivalents of $R_3MgLi$, wherein and R is $C_{1-5}$ alkyl, preferably n-butyl, in an aprotic solvent at a temperature between −40° C. to 40° C., preferably −20° C. to 0° C., more preferably 0° C., the aprotic solvent is, for example, dioxane, diethoxymethane, methylTHF, THF, diisopropylether, hydrocarbons including hexanes, heptane, isooctane, cyclohexane, xylenes, Toluene, dichloromethane, DME, MTBE, or mixtures thereof, preferably the aprotic solvent is THF;

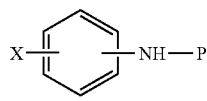

(B)

wherein X is bromine or iodine, preferably bromine, subsequently adding an electrophile E, such as, for example, $B(OCH_3)_3$, aldehydes such as $CH_3CHO$, ArylCHO, ketones such as $CH_3COCH_3$, ArylCOCH_3, halide such as $CH_2=CHCH_2Br$, $CH_3I$, or esters such as $CH_3CO_2Et$, preferably E is $B(OCH_3)_3$, further non-limiting examples of E are set forth in the table below;

to produce a compound of the formula (A)

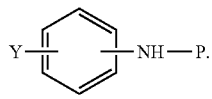

(A)

All terms as used herein in this specification, unless otherwise stated, shall be understood in their ordinary meaning as known in the art.

RT or rt—room temperature;
n-BuLi—n-Butyllithium
DME—1,2-Dimethoxyethane
THF—Tetrahydrofuran.
Boc—tert-Butoxycarbonyl.
Cbz—Benzyloxycarbonyl.
Ac—Acetyl.
Bn—Benzyl.
MeLi—methyllithium.

Unless otherwise noted, alkyl shall be understood to mean $C_{1-10}$ alkyl chain, preferably $C_{1-5}$ alkyl, branched or unbranched. An alkene is a partially unsaturated alkyl.

Ester, acyl, ketone, aldehyde and alkene shall be understood to mean an alkyl chain as herein above defined, with the respective functional group.

The term "aryl" as used herein shall be understood to mean aromatic carbocycle or heteroaryl as defined herein. Preferred carbocycles include phenyl and naphthyl. Each aryl or heteroaryl unless otherwise specified includes it's partially or fully hydrogenated derivative. For example, naphthyl may include it's hydrogenated derivatives such as tetrahydranaphthyl. Other partially or fully hydrogenated derivatives of the aryl and heteroaryl compounds described herein will be apparent to one of ordinary skill in the art.

It shall be understood, that the definitions E and Y have the following corresponding relationship as seen in the table and scheme below:

| E | Y |
|---|---|
| $B(O-C_{1-5}alkyl)_3$ | $-B(OH)_2$ |
| R'HC=O | $-CHR'-OH$ |
| $R'_2C(=O)$ | $-CR'2-OH$ |
| R'X | $-R'$ |
| $R'CO_2R'$ | $R'C(=O)-$ |
| $R'_3SnX$ | $SnR'_3$ |
| $R'_3SiX$ | $R'_3Si$ |
| $R'_2(OR')SiX$ or $(R'_2SiO)_3$ | $SiR'_2(OR')$ |

Wherein R' can be alkyl or aryl as defined herein, X is halogen and for $B(O-C_{1-5}alkyl)_3$ the $C_{1-5}$alkyl includes all $C_{1-5}$alkyl, preferably methyl, ethyl, propyl and butyl, more preferably methyl.

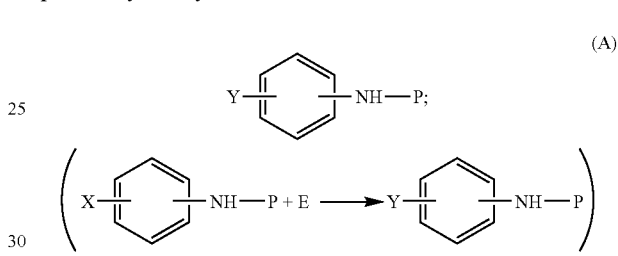

The compounds of the invention are only those which are contemplated to be 'chemically stable' as will be appreciated by those skilled in the art. For example, a compound which would have a 'dangling valency', or a 'carbanion' are not compounds contemplated by the invention.

In order that this invention be more fully understood, the following examples are set forth in the overall reaction scheme below. These examples are for the purpose of illustrating preferred embodiments of this invention, and are not to be construed as limiting the scope of the invention in any way.

EXAMPLE

Synthesis of N-Boc-4-amino-1-naphthalene Boronic Acid

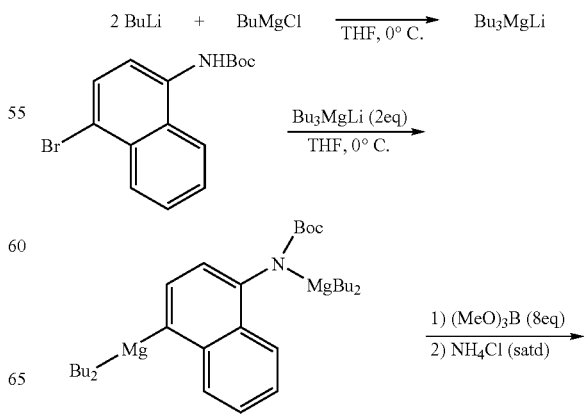

-continued

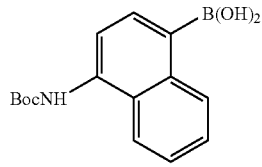

In a dry flask under Argon was added butylmagnesium chloride (2.0 M in THF, 2.0 mL, 4.0 mmol) and anhydrous THF (10 mL). The solution was cooled to −5° C. and butyllithium (1.6 M in hexane, 5.0 mL, 8.0 mmol) was added dropwise while the temperature was kept below 0° C. After the resulting solution was stirred at 0° C. for 0.5 h, the temperature was lowered to −5° C. N-Boc-4-bromo-1-aminonaphthalene (0.64 g, 2.0 mmol) was dissolved in anhydrous THF(10 mL) and added dropwise while the temperature was kept below 0° C. The solution was stirred at 0° C. for 0.5 h. HPLC of a sample taken from the solution and quenched with MeOH indicated that no starting material was left. The temperature was lowered to −5° C. and trimethyl borate(2.5 mL, 22.0 mmol) was added slowly. After the mixture was stirred at 0° C. for 2 h, ammonium chloride solution (saturated, 20 mL) was added and the mixture was stirred at 21° C. for 0.5 h. The pH of the mixture was adjusted to 7 with sodium bicarbonate and the mixture was stirred at 21° C. for 18 h. Ethyl acetate (10 mL) was added and the mixture was stirred for 0.5 h. The organic layer was separated and dried with magnesium sulfate. The solvent was removed under vacuum and then hexane (60 mL) was added and the resulting slurry was stirred for 0.5 h. Filtration and hexane (10 mL) wash gave the title compound as a white solid (0.46 g, 80.5% pure, 65% yield).

What is claimed is:

1. A process of making a compound of the formula (A):

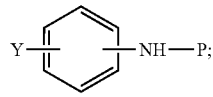

wherein
P is a nitrogen protecting group chemically suitable for Grignard reagents,
Y is defined herein below;
the phenyl ring in (A) is optionally benzo-fused to form naphthyl wherein substituents Y or NH—P can be independently at any position on each of the one or two rings, where the phenyl is not benzo-fused then substitution can be para, meta or ortho;
said method comprising, in a one pot reaction:
reacting a compound of the formula (B) with 2 equivalents of $R_3MgLi$, wherein and $R_3$ is $C_{1-5}$ alkyl, in an aprotic solvent at a temperature between −40° C. to 40° C.:

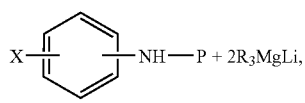

wherein X is bromine or iodine, subsequently adding an electrophile E as defined herein below,
to produce a compound of the formula (A)

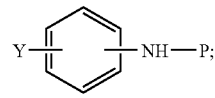

wherein E and Y have the following corresponding relationship in the table below:

| E | Y |
|---|---|
| $B(O—C_{1-5}alkyl)_3$ | —$B(OH)_2$ |
| R'HC=O | —CHR'—OH |
| $R'_2C(=O)$ | —$CR'_2$—OH |
| R'X | —R' |
| $R'CO_2R'$ | R'C(=O)— |
| $R'_3SnX$ | $SnR'_3$ |
| $R'_3SiX$ | $R'_3Si$ |
| $R'_2(OR')SiX$ or $(R'_2SiO)_3$ | $SiR'_2(OR')$ | wherein R' alkyl or aryl, X is halogen.

2. The process according to claim 1 wherein:
the formula (A) is

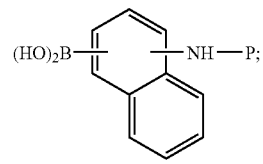

$R_3$ is n-butyl;
E is $B(O—C_{1-4}alkyl)_3$;
the temperature is between −20° C. to 0° C.;
the aprotic solvent is chosen from dioxane, diethoxymethane, methylTHF, THF, diisopropylether, hydrocarbons chosen from hexanes, heptane, isooctane, cyclohexane and xylenes, Toluene, dichloromethane, DME and MTBE, or mixtures thereof;
P is chosen from Boc, Cbz, —$CO_2Me$, —Ac, -Bn; and
X is bromine.

3. The process according to claim 2 wherein:
formula (A) is:

E is $B(O-Methyl)_3$,
the temperature is 0° C.,
the aprotic solvent is THF; and
P is Boc.

* * * * *